United States Patent [19]
Pugia et al.

[11] Patent Number: 5,846,754
[45] Date of Patent: Dec. 8, 1998

[54] ENZYME DETERMINATION WITH PROTEASE INACTIVATION

[75] Inventors: Michael J. Pugia, Granger; Robert J. Schaeper, South Bend, both of Ind.

[73] Assignee: Bayer Corporation, Elkhart, Ind.

[21] Appl. No.: 653,865

[22] Filed: May 28, 1996

[51] Int. Cl.[6] .......................................................... C12Q 1/37
[52] U.S. Cl. .................................. 435/23; 435/19; 422/56
[58] Field of Search ..................... 435/4, 19, 23, 435/975, 69.2; 422/56, 57

[56] References Cited

U.S. PATENT DOCUMENTS

| | | | |
|---|---|---|---|
| 4,657,855 | 4/1987 | Corey et al. | 435/19 |
| 5,464,739 | 11/1995 | Johnson et al. | 435/4 |

FOREIGN PATENT DOCUMENTS

| | | |
|---|---|---|
| 123902 | 9/1991 | European Pat. Off. . |
| 02131597 | 7/1989 | Japan . |
| 2131597 | 5/1990 | Japan . |
| 5176797 | 11/1993 | Japan . |

OTHER PUBLICATIONS

Cook et al., "Effect of Cu 2+ and Zn 2+ on the Inhibition of Human Leucocyte Elastase by 6–Alkyl–3–(ω–carboxy alkyl)–2–pyrones, Oleic Acid and Sulindac Sulfide," Biol. Chem. Hoppe Seyler 1989, 370, 11–19, Jan. 1989.

Pyun J., Effective Termination Method for Proteolytic Reaction Using Trypsin Immobilized on a PEI Cellulose TLC Strip, Biotechniques 19(5) 728–30, Nov. 1995.

Maunoury R., Mise en Evidence de la Centrosphere de Cellules Humaines par la Technique D'Immunoperoxydase Avec des Anticorps Naturels, Biol Cellulaire 36, 91–94, 1979.

Cook et al, Biol. Chem., vol. 370, pp. 11–19, (1989).

*Primary Examiner*—Ralph Gitomer
*Attorney, Agent, or Firm*—Jerome L. Jeffers

[57] ABSTRACT

The present invention involves a composition and method for the determination of enzymatic activity or enzyme substrate concentration in a fluid test sample in which the enzyme catalyzes a reaction in a reagent system to provide a detectable response indicative of the concentration of the enzyme or enzyme substrate in the test sample. A measured amount of a protease capable of eliminating the enzymatic activity is included in the reagent composition, so that when a measured amount of test sample is treated, the reaction producing the detectable response will have a definite end point. The invention is particularly useful in conjunction with the determination of leucocytes in urine wherein the leukocytes are lysed to release their human leucocyte elastase which hydrolyzes a chromogenic ester to provide a phenol which then reacts with a diazonium salt to form a colored azo dye.

15 Claims, No Drawings

ENZYME DETERMINATION WITH PROTEASE INACTIVATION

BACKGROUND OF THE INVENTION

Most enzyme detection methods are rate determinations rather than end point methods for reasons discussed by Kaplan et al in Clinical Chemistry, published by The C. V. Mosby Company 1984 at page 938. In general, the use of rate determinations in enzyme detection methods allows the use of lower enzyme amounts and slow turnover rates which would result in long analysis times if endpoint determinations were used. While rate determinations are preferred with instrumentation, they are difficult with visual calorimetric determinations since it is difficult to take multiple readings visually. Therefore, visual rate determinations are typically one point readings which lead to greater assay variability since the amount of color produced is dependent on time. For example, the current method for determining white blood cells (WBC) in body fluids such as urine relies on the determination of the rate of esterase activity. An esterase sample of $5.0 \times 10^{-16}$ mole/$\mu$L is detected as 10 cells/$\mu$L at 90 seconds but is detected as 2 cells/$\mu$L at 60 seconds and 16 cells/$\mu$L at 120 seconds. This time dependence leads to a high standard deviation of 7.9 cells/$\mu$L. Several approaches have been taken to endpoint enzyme detection methods. One such approach is disclosed by Shiyuku in Japanese Patent publication 5,176,797 and involves the use of hydrazine to precipitate the enzyme and endpoint the determination of cholesterol with cholesterol hydrogenase. Another approach, disclosed by Mallinckrodt in EP 123 902 is the dilution of the sample after a set time period to lower the rate of the enzymatic reaction thereby causing an endpoint in the determination of peroxidase. Another such approach is the use of multilayers to sequester the enzyme from the substrate in the determination of amylase activity as disclosed in Japanese patent publication 2,131,597. The most common approach is using inhibition of the enzyme rate as exemplified in the work of K. Oestgaard in Carbohyra. Res. 246, 229–141 1993) involving the determination of alginate lyase. Inhibition of enzyme detection methods does alter turnover rate but does not lead to a true endpoint. This behavior is reported by Cook et al based on the effect of $Cu^{2+}$ and $Zn^{2+}$ inhibition of human leucocyte elastase in Biol. Chem. Hoppe-Seyler, Vol. 370. Pp. 11–19, January 1989.

SUMMARY OF THE INVENTION

The present invention involves a method for end-pointing a determination of an enzyme or enzyme substrate in a measured amount of a fluid test sample in which the enzyme catalyzes a reaction which provides a detectable response which response is indicative of the concentration of the enzyme or enzyme substrate in the fluid test sample. The method involves including in the reagent system a measured amount of a protease capable of inactivating the enzyme to thereby terminate the detectable response and provide an end-point for the enzyme catalyzed reaction.

DESCRIPTION OF THE INVENTION

In a preferred embodiment the method of the present invention is employed in the quantitation of white blood cells (WBC) in a bodily fluid such as urine. The presence of an abnormally high level of leukocytes in a patient's urine may be indicative of pathological conditions such as kidney or urogenital tract infection. Accordingly, accurate urinary leukocyte information can be a valuable tool to the physician in the diagnosis and treatment of such pathologies. Traditionally, clinicians have relied on visual determination techniques to count the leukocyte population in urine sediment or uncentrifuged urine, a process which requires expensive equipment, e.g. centrifuges and microscopes, as well as the expenditure of considerable amounts of time in carrying out the cell count. Traditional techniques also suffer from the disadvantage that only intact cells can be detected. Leukocytes in the urinary system are subject to conditions which favor extensive cell lysis. For example, it is known that in urines of abnormally high pH, the leukocyte half life can be as short as 60 minutes. These lysed cells escape visual detection techniques, so erroneously low determinations and false negative results are problematic.

More recent techniques for the determination of leukocytes involve the detection of hydrolytic enzymes, e.g. esterases and proteases, contained within the white blood cells. These procedures utilize reagent systems which include chromogenic esters, e.g. L-alanine, lactate, valine or peptide, esters, which, when hydrolyzed by esterase or protease, produce a colored alcoholic product. Proteases such as pancreatic elastases from various animal species, $\alpha$-lytic protease of Streptomyces sp., human neutrophil cathepsin G and Streptomyces grieseus protease B and 3 would not be suitable for use in the present invention because they would tend to hydrolyze the chromogenic ester in the absence of esterase thereby creating false positive results. Some reagent systems contain accelerator compounds and diazonium salt coupling agents.

Thus, there exists in the literature a body of references disclosing the use of certain esters which, when cleaved by enzymatic activity, result in the formation of colored or other detectable species.

U.S. Pat. No. 4,637,979 discloses the use of a chromogenic ester and a diazonium salt. The ester is capable of being hydrolyzed by esterases normally present within the leukocyte to yield a phenol or a pseudophenol which can couple with the diazonium salt by a diazonium coupling reaction to form a colored azo dye. Upon lysis of the WBC, the esterase, known as human leucocyte elastase, is released, thereby initiating the hydrolysis reaction, so that the formation of the colored azo dye can take place. The intensity of the colored produced as a result of the azo dye formation is indicative of the concentration of leukocytes in the fluid being tested. This test is a quick and effective method for the determination of WBC in a body fluid such as urine. However, since the reaction is time dependent, some sort of end-pointing procedure is necessary to provide consistently accurate results if the previously mentioned drawbacks inherent in a timed reaction are to be avoided. The present invention provides a method for endpointing the reaction by including in the reagent formulation a measured amount of protease which, when contacted with the test fluid, will inactivate the esterase to thereby terminate the color forming reaction. It is necessary to use a carefully measured amount of protease in the procedure of the present invention since too much protease would abruptly destroy the esterase before any color could be formed while too little protease would not destroy enough esterase to stop color formation at the desired endpoint.

A key to successfully carrying out the present invention is the selection of a protease which is incapable of cleaving the ester but is capable of cleaving the esterase to terminate its activity. Proteases which cleave hydrophobic amino acids such as alinine would not be suitable for use in this system. In this regard, it has been discovered that trypsin XIII, a serinase protease, will give a positive result even in the absence of esterase. Since this type of false positive is, of course, to be avoided, the selection of the appropriate protease is essential. Endoproteinase XVII-B, on the other hand, will not initiate any response in the absence of esterase and is therefore suitable for use in the present invention. In general, unlike the trypsin XIII, this protease is characterized by specifically cleaving peptide bonds on the carboxyl side of aspartic and glutamic acid residues. Proteases which cleave basic amino acids may also be used.

The present invention is not limited to the above described esterase method for the determination of WBC, but can also be used to end point other assays in which an enzyme is instrumental in providing a detectable response. The selection of protease is dependent on the substrate. The above rational is for the alanine substrate. If the enzyme substrate is not an amino acid or peptide, e.g. ascorbate, the procedure is not limited as long as the protease has the ability to destroy the active site of the enzyme. This ability to destroy the enzyme's active site is dependent on whether the protease acts on the amino acids which are part of the active site and on whether the protease cleaves the amino acid inside the tertiary structure of the enzyme. Suitable analyte/enzyme combinations to which the present invention can be adopted include, but are not limited to, the following:

| Substrate | Enzyme |
|---|---|
| Cholesterol | Cholesterol oxidase |
| Glucose | Glucose oxidase |
| Ascorbate | Ascorbate oxidase |
| D-amino acids | Amino acid oxidase |
| L-Alaninine | Alanine dehydrogenase |
| beta-D-glucose | Glucose dehydrogenase |
| Nitrite | Nitrite reductase |
| hydrogen donor | Peroxidase |
| Putrescine | Putrescine acetyl transferase |
| Aspartate | Aspartate Kinase |
| Urea | Urease |
| Phenylpyruvate | Phenylpyruvate decarboxylase |
| Prophobilinogen | Porphobilinogen deaminase |
| L-alanine esters | Human leucocyte elastase |

These assays work on the principle of enzymatically generating a product which, in the presence of an indicator such as another enzyme system, produce a colored product, thereby providing a detectable response. For the use of protease end-pointing to be successful, there must be present enough protease activity to deactivate the enzyme by the desired read time but not so much protease activity that the enzyme is deactivated before any substrate turn over occurs. Thus, in the case of glucose oxidase, 1.3 IU of GO per reagent pad are enough to generate adequate color in 30 seconds when the test sample contains 100 mg/dL of glucose. If 4.3 mg/mL of endoproteinase XVII-B were included in the reagent pad, it would destroy the 1.3 IU of GO before any color could be formed. However, 0.5 mg/mL of endoproteinase would not destroy the 1.3 IU of glucose oxidase until after 30 seconds has passed, so that the colored response would be achieved.

The present invention can also be used in the determination of enzyme substrates. For example in an assay for glucose in which glucose is converted to hydrogen peroxide via glucose oxidase, hydrogen peroxide is converted into a detectable response either through direct detection or oxidation of a redox indicator to a colored product which conversion, is often catalyzed by peroxidase. The conversion of glucose to hydrogen peroxide is typically kinetic, not being fast enough to end point within a desired read time.

In general, the detection of an enzyme requires substrate therefore to be in the reagent while the detection of substrate requires the presence of enzyme in the reagent. The presence of a measured amount of protease in the reagent can inactivate the enzyme in the sample or enzyme in the reagent, depending on whether one is detecting an enzyme or enzyme substrate. In the former case, the protease and enzyme substrate are part of the reagent composition whereas in the later case, the protease and the enzyme are part of the reagent composition. The protease must not be mixed with the enzyme until the test sample is presented in order to avoid premature destruction of the enzyme. The mixing is accomplished by wetting a dry reagent with test sample or by its addition in the form of a liquid reagent.

One aspect of the present invention is directed to an analytical test strip for the detection of the enzyme in a fluid test sample, which strip comprises an absorbant carrier impregnated with the reagent system along with the protease. Suitable proteases are those which will cleave the enzyme in the reagent system to thereby cause its inactivation without reacting with the substrate with which the enzyme is designed to interact. In the following examples, human leucocyte elastase is used to demonstrate the present invention. This is a worst case enzyme because some proteases can also cleave the L-alanine ester substrate used to measure human leucocyte elastase activity which necessitates a careful selection of the protease.

The absorbant carrier used for the test strip is preferably a filter paper. Other materials useful as the absorbant carrier include felt, porous ceramic strips and woven or matter glass fibers such as those described in U.S. Pat. No. 3,846,247. Also suitable are wood, cloth, sponge material and argillaceous substances such as those described in U.S. Pat. No. 3,552,928. Alternatively, the absorbant carrier can be comprised of a nonporous material such as a polymeric film or glass. In preparation of the strip, it is typically impregnated with an aqueous solution of the protease along with a buffering system and a surfactant and dried. The strip is then impregnated with a solvent solution of the substrate for the enzyme whose concentration is being determined and any other reagents necessary for formation of the detectable responses. In the case of the WBC test previously discussed, there is included a diazonium salt indicator and a L-alanine ester to form the azo dye upon the ester being cleaved by the human leucocyte elastase released by the white blood cells. Typically, there will be included in the reagent formulation an enzyme activator such as decanol to enhance the rate of enzyme hydrolysis.

In order to ensure the release of human leucocyte elastase from the WBC, there is included in the reagent formulation a leucocyte lysing agent such as Bio-terge, or another detergent or surfactant. This material is applied to the test strip by adding the surfactant to the first or second dip solution used to prepare the strip.

While it is preferred that the reagent system be applied to an absorbant carrier and used in the strip format, a wet system in which the test fluid is contacted directly with the reagent solution can be used.

Another important aspect of the present invention is the requirement that a measured amount of fluid test sample be used in order to maintain the ratio of protease in the reagent system to substrate in the test sample in the proper range. In the case of a dry reagent system, the strip will meter the amount of test fluid it picks up. In a liquid assay, a fixed amount of fluid would be used.

The present invention is further illustrated by the following example:

EXAMPLE I

Detection of Enzyme

The WBC reagent is made from two sequential saturations of filter paper. The first saturation was with an aqueous mix containing boric acid as buffer, Bio-Terge A540 as surfactant for even color distribution, poly(vinylpyrolidone) polymer to separate the substrate and diazonium ion from the base and magnesium sulfate as moisture absorbant. The formula contained NaCl to control ionic strength. The pH of the mix was adjusted to a value of 8.8 to 9.3 using NaOH or HCl to provide an optimal pH for the enzyme to operate.

The second saturation comprised a 1-methoxy-2-propanol/1,3-dimethyl-3,4,5,6-tetrahydro-2(1H)-pyrimidione (MOP/DMPU) solvent mix containing 1-diazo-2-napthol-4-sulfonic acid (DNSA), 2-hydroxy-5-phenyl-pyrrole-N-tosyl-L-alanine ester (PPTA), and decanol. The function, preferred concentration and allowable range for use in this invention are set out in Table 1.

TABLE 1

WBC Reagent Composition

| Ingredient | Function | Prefer Conc. Used | Allowable Range |
|---|---|---|---|
| *1st application* | | | |
| Water | Solvent | 1000 mL | — |
| Bio-Terge AS40 | Surfactant | 2 g | 0–4 g/L |
| Boric Acid | Buffer | 24.7 g | 5–35 g/L |
| PVP | Polymer | 20.0 g | 5–50 g/L |
| Protease | Endpoint | 2.6 units/min. | 2.0–10 units/min |
| NaCl | Ionic Strength | 14.6 g | 2.9–43.9 g/L |
| | where a unit = 1 nM esterase destroyed | | |
| *2nd application* | | | |
| MPO | Solvent | 955 mL | — |
| DMPU | Solvent | 30 mL | 10–60 mL |
| DNSA | Diazonium indicator | 0.174 g | 0.050–0.5 g/L |
| PPTA | Enzyme substrate | 0.422 g | 0.10–0.8 g/L |
| Decanol | Enzyme activator | 15 mL | 5–40 mL/L |

The mix solutions were used to saturate filter paper, 205C grade Ahlstrom filter paper, and the paper was dried at 121° C. for 9 minutes after the first saturation and at 90° C. for 7 minutes after the second saturation. The resultant dry reagent was processed into reagent strips which were tested visually using a color chart.

Protease, either Trypsin III or Endoproteinase XVII-B was added to the test solution described above. No esterase was added. A visual response was obtained by comparing the solution to a WBC color chart having color blocks for numerical designations (ND) of 10, 20, 30 and 40 which correspond to negative, trace, small and moderate levels of WBC in urine which corresponds to 0, 25, 42 and 75 cells/$\mu$L. The results of this experiment are set out in Table 2.

TABLE 2

| Formula | Visual response in ND | |
|---|---|---|
| Protease | 20 sec | 90 sec |
| No Protease | 10 | 10 |
| Trypsin type XIII | 15 | 25 |
| Endoproteinase type XVII-B | 10 | 10 |

The test solution described above uses 2-hydroxy-5-phenyl-pyrrole-N-tosyl-L-alanine (PPTA) as the esterase hydrolyzable ester which is cleaved by the esterase enzyme present in white blood cells. After being cleaved, the PPTA can develop a color via diazonium coupling with the DNSA diazonium indicator. Since no esterase was present in the solution, no response was expected. This was the case in the experiments in which either no protease or endoproteinase XVII-B were used as indicated by the response of 10 (negative) both at 20 and 90 seconds. However, in the case of trypsin XIII as the protease, there was a positive response (15 at 20 seconds and 25 at 90 seconds) even in the absence of esterase thereby indicating that certain proteases, such as trypsin XIII can cleave the PPTA L-alanine ester linkage. Such proteases are, of course, to be avoided in the composition of the present invention due to their tendency to cause false positives.

Higher concentrations of protease result in end points being reached more quickly but also reduce response due to deactivation of enzyme before it has a chance to form the colored response. For example, 4.80 mg/mL of endoproteinase causes an endpoint at 60 seconds but reduces the visual response from that corresponding to 49 cells/$\mu$L to 16 cells/$\mu$L. In the determination of WBC, enough turnover of the PPTA ester must be achieved to match the color chart before the esterase is destroyed. Since esterase has an activity of 240 $\mu$M of PPTA/min., a turn over of approximately 100 $\mu$M PPTA is required to match the current small level of WBC in urine color block with a 42 cell/$\mu$L test sample. Therefore, the system of this example, the maximum protease activity allowed is 5.2 nM esterase/min. whereas the minimum protease activity would be at least 0.2 nM esterase/min.

Table 3 sets out the effect of protease concentration when added to the test solution containing esterase.

TABLE 3

| Formula | Amount mg/mL | Visual Response in cells/$\mu$L | | | | Standard Dev. 120 sec |
|---|---|---|---|---|---|---|
| | | 20 sec | 60 sec | 90 sec | 120 sec | |
| No protease | 0 | 25 | 42 | 59 | 117 | 21.1 |
| Endoproteinase XVII-B | 0.04 | 25 | 42 | 55 | 104 | 19.8 |
| Endoproteinase XVII-B | 0.16 | 25 | 42 | 55 | 104 | 18.7 |
| Endoproteinase XVII-B | 0.32 | 25 | 42 | 49 | 59 | 8.9 |
| Endoproteinase XVII-B | 1.28 | 25 | 42 | 49 | 49 | 4.3 |
| Endoproteinase XVII-B | 4.80 | 0 | 15 | 16 | 16 | 2.1 |

The visual response of WBC was measured against a standard color chart having standard colors for 0, 25, 42, 75 and 200 cell/$\mu$L. The tested solutions contained 2.6 nM esterase which corresponds to 42 cell/$\mu$L$_i$, the pH was maintained at 5.2. From Table 3 it can be determined that the protease concentration of 4.8 mg/mL reduced the 42 cell/$\mu$L WBC response to 16 cell/$\mu$L demonstrating the upper limit of the concentration. The protease concentration of 0.16 mg/mL did not lead to an endpoint thereby demonstrating the lower limit of the effective concentration of protease in this example.

EXAMPLE II

Detection of Substrate

A glucose reagent system was prepared from one saturation of filter paper. The saturation solution contained citric acid as buffer, potassium iodide as indicator, poly (vinylpyrolidone) polymer to stabilize the reagent color, peroxidase as a catalyst for detecting hydrogen peroxide and glucose oxidase for the generation of hydrogen peroxide when glucose is present in the test sample. The pH of the mix was adjusted to a value of 6.0 to 6.5 using NaOH or HCl to provide an optimal pH for the enzyme to operate. The function, preferred concentration and allowable range for each of the reagents used in this system are set out in Table 4.

TABLE 4

Glucose Reagent Composition

| Ingredient | Function | Preferred Concentration | Allowable Range |
|---|---|---|---|
| water | solvent | 1000 mL | — |
| citric acid | buffer | 400 mM | 200–800 mM |
| PVP | polymer | 0.5% | 0.2–3.0% |
| KI | indicator | 7 g/dL | 1–14 g/dL |
| peroxidase | enzyme | 3300 IU | 1000–5000 IU |
| glucose oxidase | enzyme | 1.3 IU | 1.0–5.0 IU |

The mix solution was used to saturate Whatman 3 MM grade filter paper after which the paper was dried at 100° C. for 15 minutes. The resultant dry reagent was processed into strips which were tested visually using a color chart.

As shown in Table 5, the addition of endoproteinase XVII-B to the glucose oxidase reagent allows an endpoint to be achieved. The end point is demonstrated by the result at 20 seconds equaling the result at 180 seconds when the protease is present. The reagent's were visually read to the nearest color level using color standards made at 0, 100, 250, 500 and 1000 mg/dL glucose.

TABLE 5

Affect of Protease Added to the Reagent for Detecting Glucose

| Formula | Amount mg/mL | Visual Response in mg/dL Glucose | | |
|---|---|---|---|---|
| | | 20 sec | 60 sec | 180 sec |
| No protease | 0 | 100 | 250 | 500 |
| Endoproteinase XVII-B | 0.5 | 100 | 100 | 100 |

We claim:

1. In a method for the determination of enzymatic activity in a fluid test sample wherein an enzyme catalyzes a reaction in a reagent system to provide a detectable response indicative of the concentration of the enzyme or enzyme substrate in the fluid test sample, the improvement which comprises adding a measured amount of the fluid test sample to a measured amount of a protease capable of inactivity the enzyme responsible for producing the detectable response which does not inactivate the reagent system which provides the detectable response so that the reaction which provides the detectable response ceases after a predetermined time which time is determined by the concentration of the protease in the reagent system.

2. The improvement of claim 1 wherein the enzyme which catalyzes the reaction to provide a detectable response is an esterase and the reagent system comprises a diazonium salt and an ester which is hydrolyzed by the esterase to yield a phenol or a pseudophenol which is capable of coupling with the diazonium salt to provide the detectable response by the formation of a colored azo dye.

3. The improvement of claim 1 wherein the enzyme substrate is glucose and the enzyme is glucose oxidase.

4. In a composition for the determination of leukocytes in a measured amount of an aqueous test fluid by measuring the amount of esterase released upon lysis of the leukocytes which composition comprises a diazonium salt and an ester which is hydrolyzed by the esterase to yield a phenol or a pseudophenol which couples with the diazonium salt by a diazonium coupling reaction to form a colored azo dye wherein the intensity of the color is indicative of the concentration of leukocytes in the aqueous test fluid, the improvement which comprises including a measured amount of a protease, which does not cleave the ester but cleaves the esterase in the composition, so that the color forming reaction between the diazonium salt and phenol or pseudophenol ceases after a predetermined time which time is determined by the concentration of the protease in the composition.

5. The improvement of claim 4 wherein the leukocytes are lysed by the inclusion of a surfactant in the composition.

6. The improvement of claim 4 wherein the esterase is human leucocyte elastase.

7. The improvement of claim 4 wherein the protease is selected from proteases which cleaves peptide bonds on the carboxyl side of aspartic acid and glutamic acid residues.

8. The method of claim 4 wherein the aqueous test fluid is urine.

9. The method of claim 4 wherein the protease is endoproteinase XVII-B.

10. A test strip for the determination of enzymatic activity or amount of enzyme substrate in a fluid test sample which comprises an absorbent carrier as the strip material which absorbs a measured amount of the fluid test sample when contacted therewith having absorbed therein a buffering agent and an enzyme substrate which will provide a colored detectable response upon exposure to the enzyme in the fluid test sample together with a measured amount of a protease which inactivates the enzymatic activity but does not cause the detectable response in the enzyme substrate, so that the reaction which provides the colored detectable response ceases after a predetermined time which time is determined by the concentration of the protease in the reagent system.

11. A method of measuring enzymatic activity in a fluid test sample which comprises contacting the strip of claim 10 with the fluid test sample and determining the enzymatic activity by observing the magnitude of the detectable response.

12. The method of claim 11 in which the fluid test sample is urine and the enzymatic activity is derived from human leucocyte elastase which is released from leucocytes contained in the urine by lysing of the leucocytes by a lysing agent absorbed to the absorbent material of the test strip.

13. The method of claim 12 wherein the detectable response is a result of a hydrolysis of a chromogenic ester being hydrolyzed by the human leucocyte elastase to yield a phenol which couples with a diazonium indicator present in the reagent system to form a colored azo dye.

14. The method of claim 13 wherein the diazonium indicator is 1-diazo-2-napthol-4-sulfonic acid, the ester is 2-hydroxy-5-phenyl-pyrrole-N-tosyl-L-alanine ester and the lysing agent is a surfactant.

15. The method of claim 14 wherein the proteinase is endoproteinase XVII-B.

* * * * *